(12) United States Patent
Klass et al.

(10) Patent No.: US 8,744,873 B2
(45) Date of Patent: Jun. 3, 2014

(54) METHOD AND SYSTEM FOR MONITORING PATIENT CARE

(71) Applicant: VigiLanz Corporation, Minnetonka, MN (US)

(72) Inventors: David B. Klass, Westchester, IL (US); Adam P. Klass, Oak Park, IL (US); Dennis J. Ring, Shakopee, MN (US); David Goldsteen, Minneapolis, MN (US)

(73) Assignee: VigiLanz Corporation, Minneapolis, MN (US)

( * ) Notice: Subject to any disclaimer, the term of this patent is extended or adjusted under 35 U.S.C. 154(b) by 0 days.

(21) Appl. No.: 13/894,023

(22) Filed: May 14, 2013

(65) Prior Publication Data

US 2013/0246100 A1   Sep. 19, 2013

Related U.S. Application Data

(63) Continuation of application No. 13/426,691, filed on Mar. 22, 2012, now Pat. No. 8,457,985, which is a continuation of application No. 11/754,798, filed on May 29, 2007, now Pat. No. 8,160,896, which is a continuation of application No. 10/175,345, filed on Jun. 18, 2002, now abandoned, which is a continuation-in-part of application No. 09/970,320, filed on Oct. 3, 2001, now Pat. No. 6,993,402.

(60) Provisional application No. 60/272,019, filed on Feb. 28, 2001.

(51) Int. Cl.
*G06Q 10/00* (2012.01)

(52) U.S. Cl.
USPC ................ 705/2; 705/3; 600/300; 600/483

(58) Field of Classification Search
USPC .............. 705/2, 3; 600/300, 483; 706/45, 46; 726/4; 604/503
See application file for complete search history.

(56) References Cited

U.S. PATENT DOCUMENTS 4,731,725 A * 3/1988 Suto et al. ................... 706/46
4,974,607 A * 12/1990 Miwa .......................... 600/483

(Continued)

FOREIGN PATENT DOCUMENTS

EP    0 917 078 A1    5/1999
EP    1 237 113 A2    9/2002

(Continued)

OTHER PUBLICATIONS

Shabot, M.M. et al. "Wireless Clinical Alerts for Critical Medication, Laboratory and Physiological Data," Proceeding of the 33rd Hawaii International Conference on System Sciences, Jan. 4, 2000, pp. 1533-1538.

(Continued)

*Primary Examiner* — Dilek B Cobanoglu
(74) *Attorney, Agent, or Firm* — Kenneth E. Levitt; Dorsey & Whitney LLP

(57) ABSTRACT

The subject invention is a Patient Care Monitoring System which employs a novel method and system for monitoring the care provided to a patient at a health care facility. In one embodiment, the subject invention includes a central processor in communication with a health care facility's computer systems, receiving data therefrom. This data is arranged and correlated to enable the subject invention to filter through the data and detect if a particular treatment, diagnostic test, or course of action has been or is in danger of being overlooked.

3 Claims, 7 Drawing Sheets

(56) References Cited

U.S. PATENT DOCUMENTS

| | | | |
|---|---|---|---|
| 5,348,008 A | | 9/1994 | Bornn et al. |
| 5,473,537 A | * | 12/1995 | Glazer et al. ............... 600/300 |
| 5,517,405 A | * | 5/1996 | McAndrew et al. ........... 706/45 |
| 5,672,154 A | * | 9/1997 | Sillen et al. ................. 604/503 |
| 5,827,180 A | | 10/1998 | Goodman |
| 6,000,828 A | * | 12/1999 | Leet ............................... 705/2 |
| 6,076,166 A | * | 6/2000 | Moshfeghi et al. ............. 726/4 |
| 6,081,786 A | * | 6/2000 | Barry et al. ..................... 705/3 |
| 6,277,071 B1 | * | 8/2001 | Hennessy et al. ........... 600/300 |
| 6,356,873 B1 | | 3/2002 | Teagarden et al. |
| 6,731,989 B2 | | 5/2004 | Engleson et al. |
| 6,993,402 B2 | | 1/2006 | Klass et al. |
| 8,160,896 B2 | | 4/2012 | Klass et al. |
| 2002/0040282 A1 | | 4/2002 | Bailey et al. |
| 2002/0095313 A1 | | 7/2002 | Haq |
| 2003/0028811 A1 | | 2/2003 | Walker et al. |
| 2003/0172081 A1 | | 9/2003 | Dulong et al. |

FOREIGN PATENT DOCUMENTS

| | | |
|---|---|---|
| JP | 03-218741 | 9/1991 |
| JP | 08-272882 | 10/1996 |
| JP | 08-315040 | 11/1996 |
| JP | 11-282934 | 10/1999 |
| WO | WO 99-10821 | 3/1999 |
| WO | WO 01-86506 A1 | 11/2001 |

OTHER PUBLICATIONS

Leyerle, B.J. et al. "The PDMS as a Focal Point for Distributed Patient Data," International Journal of Clinical Monitoring and Computing, vol. 5, No. 3, 1988, pp. 155-161.

Luchins, Daniel J. et al. "Computerized Monitoring of Valproate and Physician Responsiveness to Laboratory Studies as a Quality Indicator," Psychiatric Services, Sep. 2000, vol. 51, No. 9.

* cited by examiner

METHOD AND SYSTEM FOR MONITORING PATIENT CARE

CROSS-REFERENCE TO RELATED APPLICATION(S)

This application is a continuation of U.S. patent application Ser. No. 13/426,691, filed on Mar. 22, 2012, which issued as U.S. Pat. No. 8,457,985; which is a continuation of U.S. patent application Ser. No. 11/754,798, filed on May 29, 2007, which issued as U.S. Pat. No. 8,160,896; which is a continuation of U.S. patent application Ser. No. 10/175,356; which is a continuation-in-part of U.S. patent application Ser. No. 09/970,320, filed on Oct. 3, 2011, which issued as U.S. Pat. No. 6,993,402; which claims priority to U.S. Provisional Patent Application No. 60/272,019, filed on Feb. 28, 2001, the entire contents of all of which are hereby incorporated herein by reference in their entirety.

TECHNICAL FIELD

This invention relates to a method and system for monitoring patients in a health care facility. More particularly, the invention relates to a method and system for integrating and using data from a medical facility's computer systems to monitor the care being provided to a patient.

BACKGROUND OF THE INVENTION

A health care facility will typically have hundreds of standard procedures, protocols, rules, or guidelines dealing with the treatment and care provided to a patient. Pharmaceutical and medical device companies will also typically prescribe a regimen of care for a patient who uses their products. In addition, state and federal regulatory commissions, insurance companies, and even medical organizations will also prescribe additional standards for the care of patients.

With all these procedures, protocols, rules, or guidelines, it is quite difficult for a health care practitioner to keep up with or even remember the countless procedures which should be followed. Typically, a health care practitioner will treat a number of patients each day, and in the course of treating that patient, a number of different procedures or protocols may need to be applied. As a result, some procedures, protocols, or guidelines may be overlooked or simply forgotten, and the patient may not receive the optimum level of care.

A health care facility will often use patient charts to track the care provided to each patient. Each patient chart will typically include annotations for all treatments and medications for a particular patient. The health care practitioner is expected to read the chart, and from that information, know the exact regiment of care that should be provided, and to execute the regiment in a timely fashion. However, the charts do not remind the health care practitioner that a proper procedure was followed, nor will it suggest a regiment of treatment, nor will it remind the health care practitioner that a particular action is due. As such, the current method of tracking and monitoring patient care does not provide adequate assurances that a patient is being treated according to a given health care organization's guidelines.

The health care practitioner is also faced with numerous situations wherein they are entrusted with the timely application of medical care. For example, a patient may receive an abnormally high level of white blood cells seeming to indicate a possible infection. The guidelines for treating the infection may call for the periodic application of an antibiotic medication and continued monitoring of the white blood cell level. Failure of a health care practitioner to give the appropriate medication at the required interval of time may lengthen the period of illness or even make the treatment less effective. A failure to monitor the white blood cell level may result in the overprescribing or underprescribing the appropriate amount of medication. Consequently, the timely application of medical care is a vital concern to a health care facility.

However, the number of patients being treated, the wide variety of procedures and protocols to follow, and time constraints make it difficult for a health care practitioner to remember which specific therapeutic intervention or diagnostic test is indicated for a specific decision state or intervention. As a result, treatments and diagnostic tests may be missed simply because the health care practitioner had forgotten that it was indicated.

What is needed is a method of tracking and monitoring the care given a patient to ensure that the patient is being provided the optimum level of care. Furthermore, there is also a need for a method and a system for reminding the health care practitioner when a prescribed action has been overlooked or needs to be performed.

BRIEF SUMMARY OF THE INVENTION

Accordingly, the subject invention is a Patient Care Monitoring System which employs a novel method and system for monitoring the care provided to a patient at a health care facility. In one embodiment, the subject invention includes a central processor in communication with a health care facility's computer systems, receiving data therefrom. This data is arranged and correlated to enable the subject invention to filter through the data and detect if a particular treatment, diagnostic test, or course of action has been or is in danger of being overlooked.

At the core of the subject invention is a set of rules that specify characteristics of established Practice Guidelines within the hospital. A Practice Guideline is a set of clinical parameters that reflects a specific event or situation in which decision making and/or action may be appropriate. These rules can be defined and tailored by the health care facility to meet its specific needs.

In one embodiment, each rule defines four categories of parameters: a Rule Criterion defines the drug or lab condition to monitor; a Response Criterion defines the set of recommended drug and/or lab responses; a Practice Interval defines how long the subject invention waits for a predefined clinical response and a Reminder Notification if the acceptable response criteria is not satisfied within the Practice Interval.

In one embodiment, each rule monitors for either a Target Lab condition or a Target Drug condition. Lab Practice Guideline rules and Drug Practice Guideline rules are handled differently. Minimally, in order to satisfy a Lab Practice Guideline rules, a Target Lab test must have been taken, and the result of that test must be within a pre-defined range. To minimally satisfy a Drug Practice Guideline rule, the patient must have been administered a Target Drug.

Once the Practice Guideline is minimally satisfied, the subject invention will then filter the patient data for associated drugs, associated labs, or additional patient filters. Through the use of associated drugs and labs, the Practice Guideline rules can be defined to address sophisticated conditions. Each Practice Guideline rule can specify that a patient must concurrently be on specific medication or must have had specific lab tests with values within a certain range.

The subject invention also includes a warning system which notifies the health care practitioner that an established clinical guideline is not being followed, thereby permitting corrective intervention prior to the end of the Practive Interval. Once a Rule Criterion is met, the subject invention establishes an interval to wait for the expected clinical response. During this interval, the subject invention monitors for new drug orders and lab tests for the patient. If the new drug orders and lab tests satisfy the Response Criteria, then no Reminder is issued. If the response criterion has not been satisfied a Reminder is issued near the end of the Practice Interval. The dynamic nature of the Practice Interval is a unique feature of the invention. A function can be activated such that the interval shortens when the lab test results approach a pre-determined control level. Conversely, the interval lengthens if the lab test results indicate an improving situation.

While several embodiments are disclosed, still other embodiments of the present invention will become apparent to those skilled in the art from the following detailed description. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

A. General Overview

Figure 1:
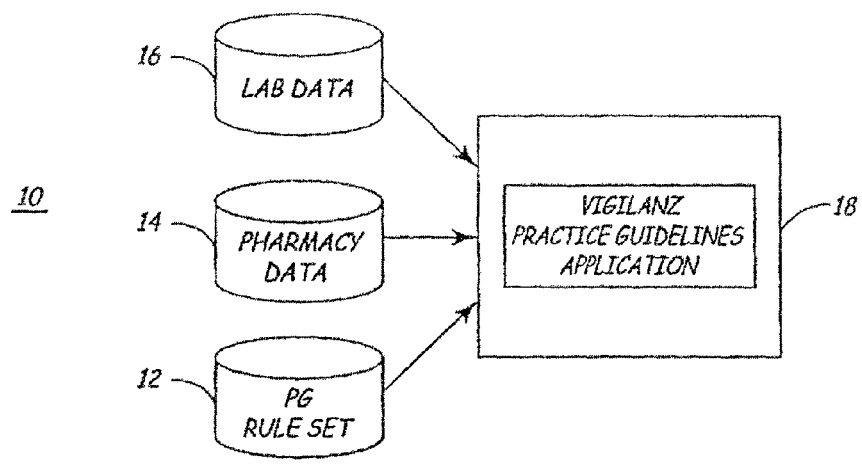
FIG. 1 is a block diagram representing an embodiment of a Patient Care Monitoring System.

As shown in FIG. 1, the subject invention is a Patient Care Monitoring System 10 that employs a novel method and system for monitoring the care provided to a patient at a health care facility. In one embodiment, the subject invention includes a central processor in communication with a health care facility's computer systems and receiving patient data therefrom. Once received, this data is arranged and correlated to enable a search engine to filter through the data and detect if a particular treatment or course of action has been or is in danger of being overlooked.

For the purposes of explanation only, the disclosed embodiment is comprised of a system which retrieves data from a health care facility's Pharmacy and Laboratory computer system. This embodiment monitors drug orders and lab tests transmitted therefrom to detect exceptions to rules established or adopted by a health care facility as optimal practice norms. It can be appreciated by a person skilled in the art, that the subject invention is easily adaptable to gather data from a number of other data sources in the health care facility such as a patient data management system, a patient physiological monitoring system, medical devices, and a patient medical records system. It can also be appreciated that the subject invention is also easily adapted to monitor a number of different clinical practices or even patient physiological data in order to determine when clinical guidelines have not been followed.

Prior to the use of the Patient Care Monitoring System 10, Practice Guideline Rules are created and stored within the Practice Guideline Rule database 12. Each rule contains a plurality of data fields therein which contain information that is used by the Patient Care Monitoring System 10 to determine if a deviation from the practice guidelines has occurred.

In one embodiment, information within pharmacy 14 and lab 16 data are extracted from transmissions emanating from a health care facility's pharmacy and laboratory information systems. This data is then placed into a normalized drug table or a normalized lab table respectively. The data within these tables are then filtered by a Practice Guidelines search engine that searches the Practice Guideline database 12 to see if it matches any predefined Practice Guidelines Rules.

In one embodiment, each Practice Guideline Rule defines four categories of parameters: a Rule Criterion defines the drug or lab condition to monitor; the Response Criteria defines the set of recommended drug and/or lab responses; the Practice Interval defines how long the subject invention waits for a predefined clinical response and a Reminder Notification that issues if a response criteria is not satisfied within the Practice Interval.

In one embodiment, if the Rule Criteria are satisfied, the subject invention establishes an interval to wait for the expected clinical response. During this interval, the subject invention monitors for new drug orders or lab tests for the patient. If new drug orders or lab tests satisfy the Response Criterion, then no Reminder is issued for the patient, however, if the response criterion has not been satisfied during the Guideline Interval, a Reminder is issued warning the health care practitioner. By applying predefined Practice Guideline Rules to the pharmacy 14 and lab 16 system data, the subject invention is able to identify when predefined clinical guidelines are not being followed for a particular patient. This early warning provides valuable time for corrective clinical action to be taken.

B. System Configuration

Figure 2:
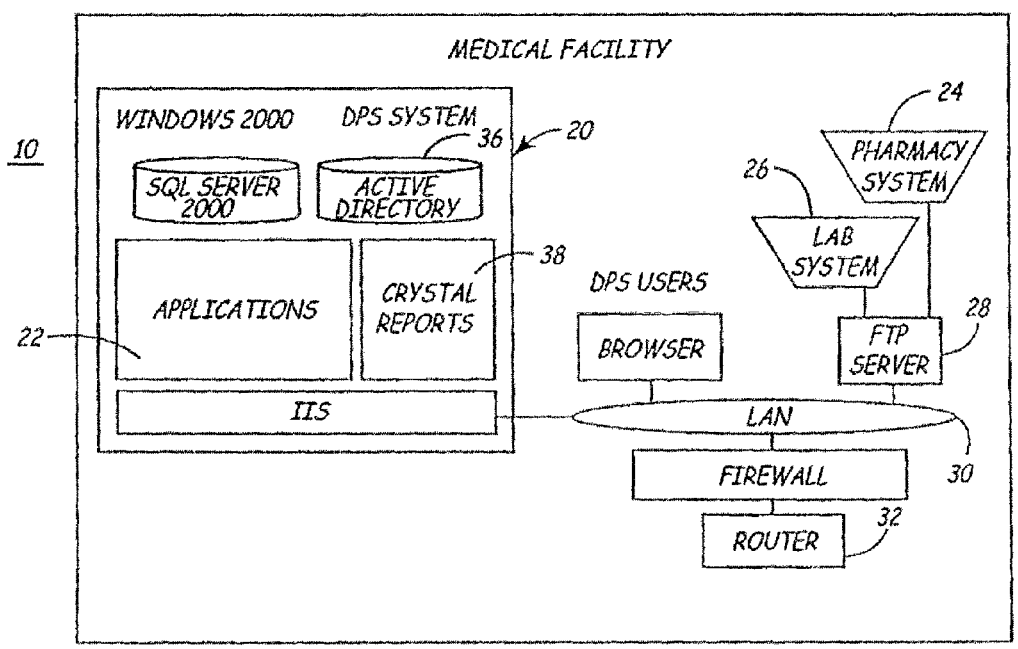
FIG. 2 is a diagram representing the hardware components of the Patient Care Monitoring System of FIG. 1.

As shown in FIG. 2, an embodiment of a Patient Care Monitoring System 10 in accordance with the subject invention is shown. This embodiment is comprised of a central processor 20 having included therein a number of task oriented applications. The central processor 20 can be any computer known to those skilled in the art, including standard attachments and components thereof (e.g., a disk drive, hard drive, CD/DVD player or network server that communicates with a CPU and main memory, a sound board, a keyboard and mouse, and a monitor). The processor of the CPU in the computer may be any conventional general-purpose single- or multi-chip microprocessor. In addition, the processor may be any conventional special purpose processor such as a digital signal processor or a graphics processor. The microprocessor can include conventional address lines, conventional data lines, and one or more conventional control lines.

In one embodiment, the central processor 20 includes software applications 22 or computer instructions. As will be explained further below, and more specifically in the sections pertaining to their function, the applications 22 coordinate the functional components of the Patient Care Monitoring System 10. These applications 22 may include known software components that are commercially sold, as well as proprietary applications specifically developed to perform specific functions in the Patient Care Monitoring System.

As shown in FIGS. 1 and 2, in one embodiment, the subject invention is configured to operate in a stand-alone environment, located within a health care facility. It is configured to operate on a dedicated computer system that is in communication via a computer network with a health care facility's Pharmacy 24 and Laboratory 26 Information Systems. Patient data from laboratory 26 and pharmacy 24 information systems may be compiled and transmitted by a FTP server 28 through a Local Area Network (LAN) 30. The health care facility's input can be "batched" and transmitted periodically as files, or it can be sent continuously as transactions.

Alternatively, the data from Laboratory 26 and Pharmacy 24 information systems may be compiled and transmitted to the Patient Care Monitoring System 10 by a File Transfer Protocol ("FTP") server 28 through a router 32 in communication with the Patient Care Monitoring System 30 via a computer network such as a secure intranet or a LAN. In other embodiments, telephonic means or even direct hard wire connections can be utilized for transmitting data to the Patient Care Monitoring System 10. The data transfers are typically initiated by a medical facility, and can be transmitted periodically or may be transferred dynamically as the data is created.

Figure 3:
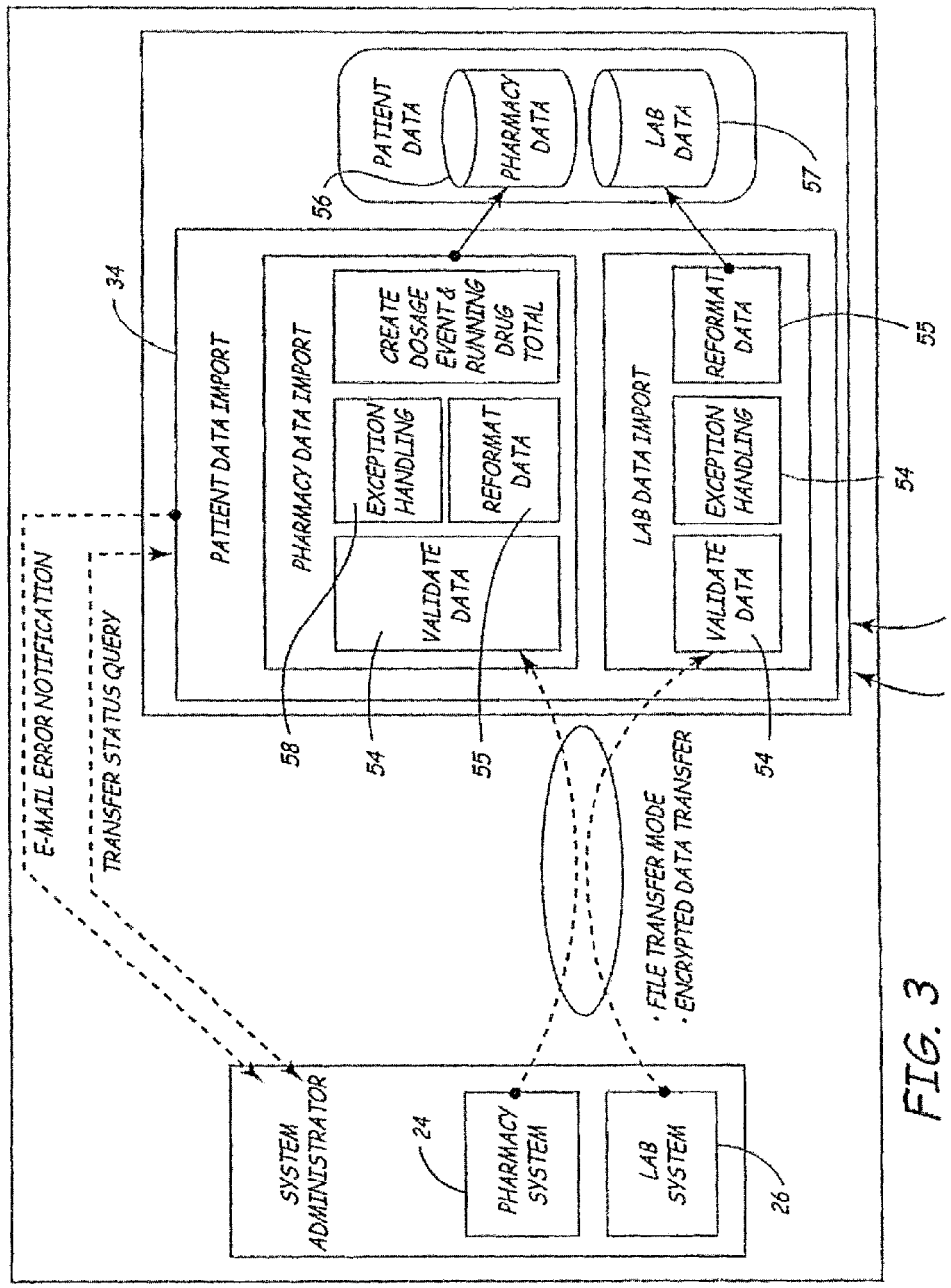
FIG. 3 is a block diagram representing one embodiment of a data import procedure.

As shown in FIGS. 1 and 3, in one embodiment, the Patient Care Monitoring System 10 includes a number of applications 22 to perform a number of functions. A Patient Data Import Application 34 is included to receive, validate, and format pharmacy and lab data received from a medical facility. A User Access Application may also be included for limiting access to the Patient Care Monitoring System 10 to authorized individuals and for limiting access to information. The User Access Application typically works in conjunction with a User Directory 36 located on a directory server. The User Directory 36 is comprised of a database of authorized users and a level of accessibility allowed for each. The User Access Application can be any that is known in the art. An Administration Application may also be included for organizing and maintaining databases pertaining to particular medical facilities and users. A known report generation application 38 such as Crystal Reports may also be included.

C. Importing Data

As shown in FIG. 3, in one embodiment, data records from a health care facility is transmitted to the Patient Care Monitoring System through a direct interface with the Pharmacy System 24 and the Laboratory System 26. The Patient Care Monitoring System 10 first subjects the data record to a validation process (block 54) to verify that the data record is in a known format and to verify that it is complete. Once the data record is verified, it is then reformatted by a reformatting process (block 55) to be compatible with data structure employed by a database wherein the data is stored.

If an error occurred in the transmission of the data record or if the data record is improperly formatted, an exception handling procedure (block 58) is triggered. The exception handling procedure (block 58) includes the steps of creating an error message and posting it on an error log which notes the time and date of the error.

A pharmacy information system 24 will typically provide the Patient Care Monitoring System 10 with pharmacy data for each patient and a laboratory information system 26 typically provides information pertaining to lab tests. A data record imported from a pharmacy information system 24 will typically include information pertaining to a medication prescribed to a patient and the logistics as to how the medication is to be administered. A data record from a lab information system 26 typically provides data pertaining to lab tests for each patient. Lab or pharmacy data is extracted from their respective data records and this data is then correlated with records pertaining to the same patient ID, and stored within a database. In this embodiment, a pharmacy database 56 stores pharmacy data and a laboratory database 57 stores laboratory data.

The data record can be an ASCII file or it can be formatted in any known manner. A pharmacy data record will typically include data fields containing a patient ID, a doctor ID, the drug administered, a dosage, a time of dosage, a begin date, and a discontinuance date. A lab data record will typically include data fields for a patient ID, a doctor ID, a lab test performed, the test result, the date and time of the test.

In one embodiment, a normalized table called a daily record is created from data extracted from a pharmacy data record and stored within the pharmacy database 56. The table is comprised of a chronological sequence of records, with each record having data fields identifying a drug, a drug dosage given or to be given, and a time and date when the drug dosage is administered or will be administered. Each record also includes a data field which represents the total dosage for a particular drug within a 24 hour period from the time the drug is or will be given. A new record is created with each drug dosage given or each drug dosage to be given, and the daily record is updated with each new record.

A normalized lab table is also created from lab data and stored within the laboratory database 57. The table is also comprised of a chronological sequence of data records, with each data record having data fields identifying a patient ID, a time of the test, the lab name, and the lab result. A new record is created for every test result, and the lab table is updated after the creation of each new record.

D. Practice Guidelines

Figure 4:
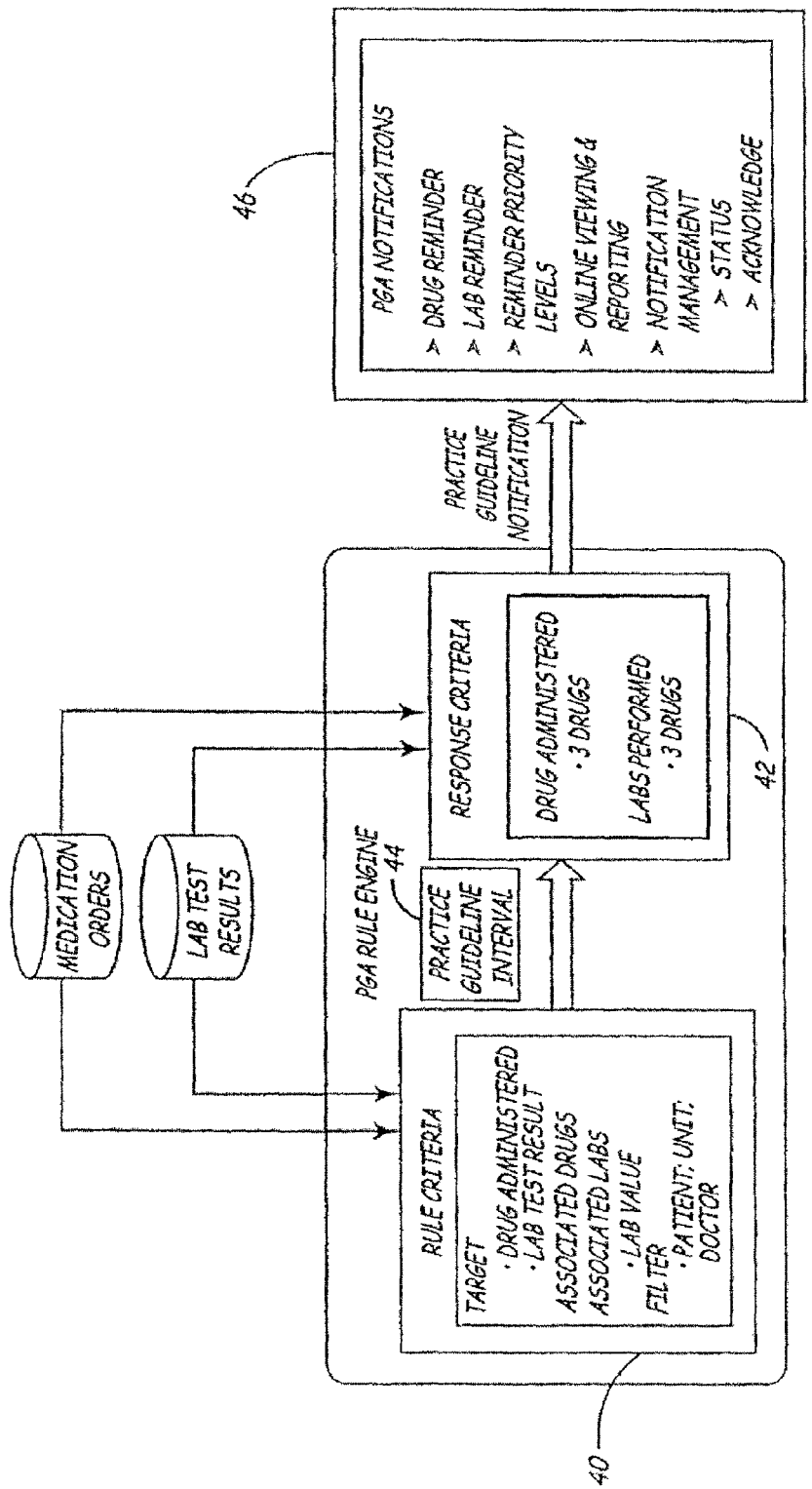
FIG. 4 is a diagram representing the flow of data in one embodiment of the subject invention.

As shown in FIG. 4, at the core of the subject invention is a set of Practice Guideline Rules that identifies characteristics of established clinical practices within or Preventive Guidelines adopted by the hospital. A Practice Guideline Rule is a set of clinical parameters that reflects a specific event or situation in which decision making and/or action may be appropriate. These rules can be defined and tailored to meet the specific needs of each hospital.

Prior to the use of the Patient Care Monitoring System 10, Practice Guideline Rules are created and stored within the Practice Guideline Rule database. Each Practice Guideline Rule contains a plurality of data fields therein which contain information that is used by the Patient Care Monitoring System 10 to determine if a deviation from the practice norms has occurred. The values which are contained in each data field are either defined by or approved by a health care practitioner utilizing the Practice Guideline Rules.

In one embodiment, each Practice Guideline Rule defines four categories of parameters: a Rule Criterion 40 defines a drug or lab condition to monitor; a Response Criterion 42 defines a set of recommended drug and/or lab responses; a Practice Interval 44 defines how long the subject invention waits for a predefined clinical response and a Reminder Notification 46 to warn a health care practitioner that an acceptable response criteria has not been satisfied.

Figure 5:
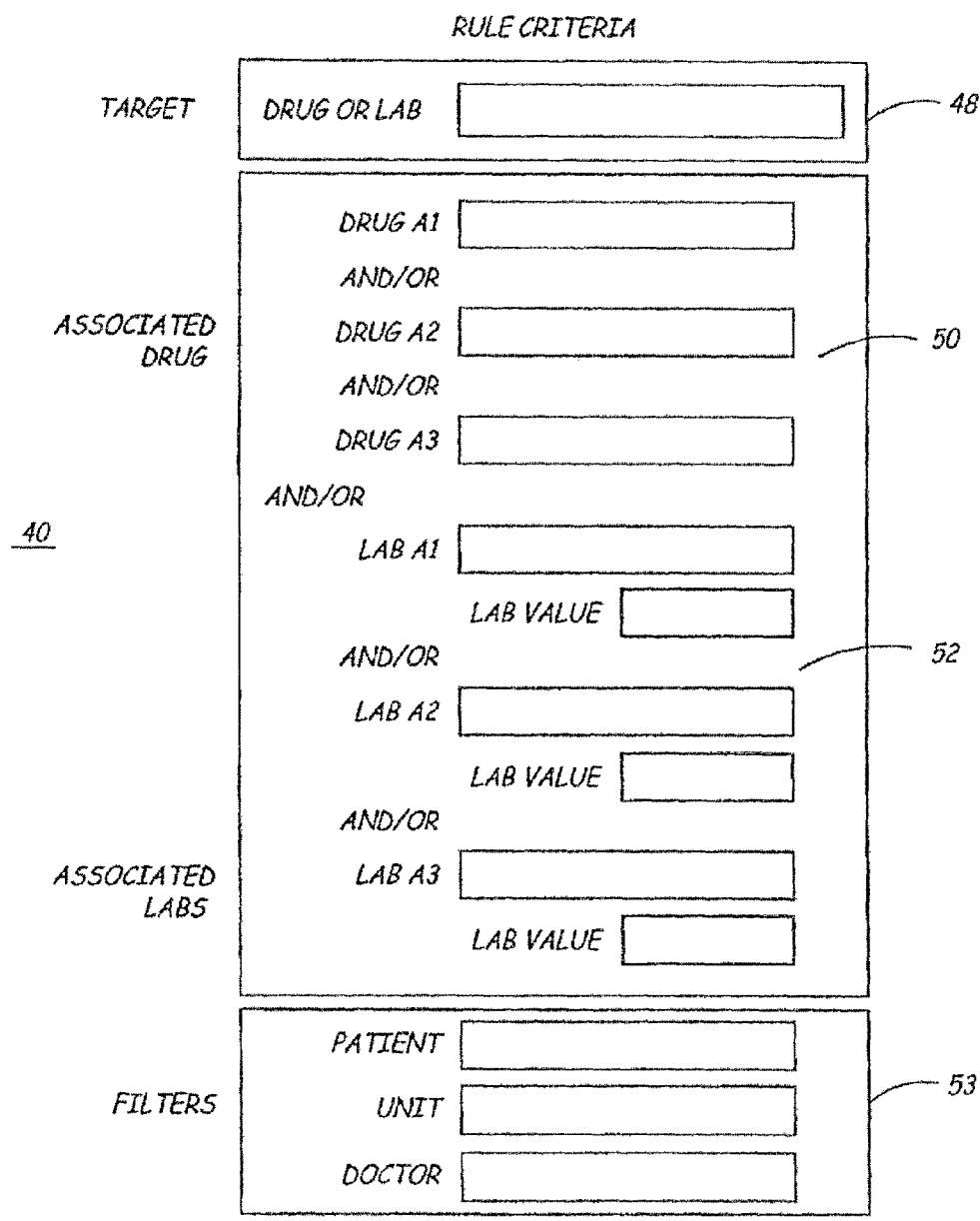
FIG. 5 is one embodiment of a data field for a rule criteria.

As shown in FIG. 5, the rule criterion 45 will include a target variable 48 which comprises the initial filter for a practice guideline, a plurality of associated variables, and additional filters 53. In one embodiment, the target variable 48 can be either a Target Lab and its value or a Target Drug. The associated variables can include an associated drug 50 or an associated lab 52. The additional filters 53 can include a patient name, the patient's location within a health care facility (unit), and a patient's doctor. Depending upon the health care facility, a number of other criteria can be inserted as additional filters 53.

In one embodiment, up to three associated drugs 50 can be specified. These drugs can be defined with an "and/or" operand. If the "and" condition is specified, then all the associated drug must be administered. If the "or" condition is specified, then only one of the associated drugs is required to satisfy the rule criterion 40. Similarly, up to three associated labs 52 can also be specified. The same type of "and/or" operand is defined for each lab test. In addition, for associated labs 52, the Rule can specify the value of the lab test result. The lab tests can be for either numeric or positive/negative lab test results.

Figure 6:
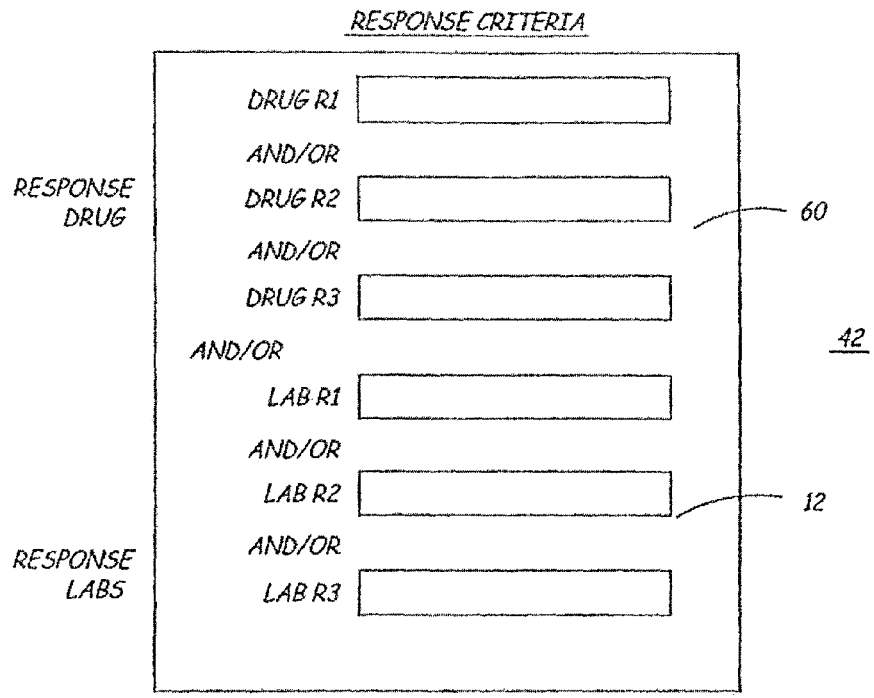
FIG. 6 is one embodiment of a data field for a response criteria.

As shown in FIG. 6, in one embodiment, the response criteria 42 includes both the administering of drugs 60 and/or new lab tests 62. Through the use of these Response Drugs 60 and Response Labs 62, the subject invention can identify whether an acceptable response or an acceptable set of responses have been undertaken in response to the presence of the Target Variable.

In one embodiment, up to three Response Drugs 60 can be specified. These drugs can be defined with an "and/or" operand. If the "and" condition is specified, then all of the drugs must be administered to satisfy the Rule Criterion 40. If the "or" condition is specified, then only one of the drugs must have been administered to satisfy the Rule Criterion 40. Similarly, up to three Response Labs 62 can be specified in a response criteria. The same type of "and/or" operand is defined for each lab test.

Figure 7:
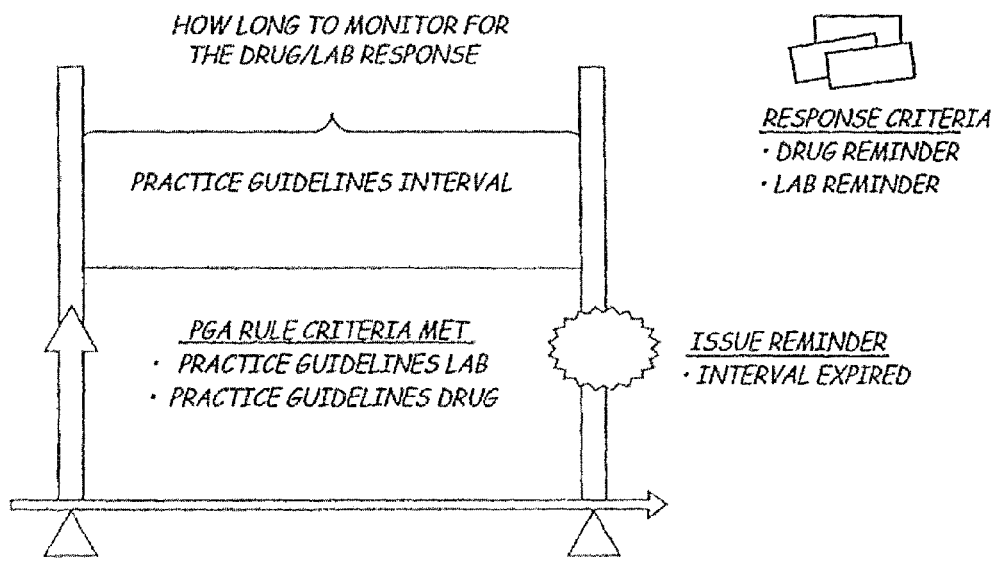
FIG. 7 is a diagram explaining one embodiment of the Practice Guidelines interval.

As shown in FIG. 7, in one embodiment, the Practice Interval 44 contains a fixed response interval that specifies the number of hours to monitor patient data for the Response Criteria and a nearness indicator that specifies when the notification should be issued in relation to the fixed response interval. In addition, if the target variable is a target lab, the Practice Interval 44 can include modifiers that will dynamically adjust the fixed interval based upon the Target Lab test results.

Figure 8:
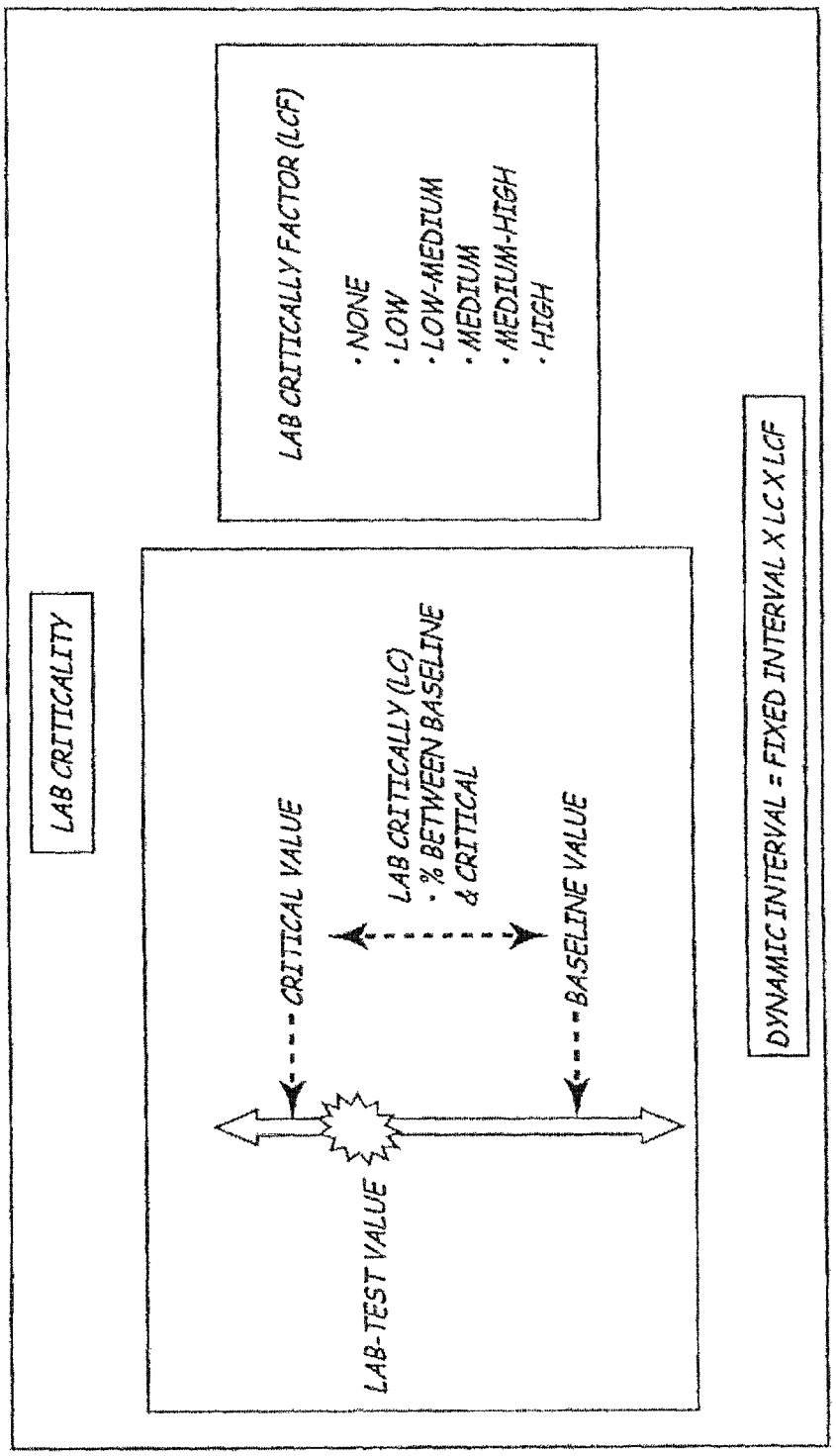
FIG. 8 is a diagram of one embodiment for calculating a dynamic interval.
Figure 9:
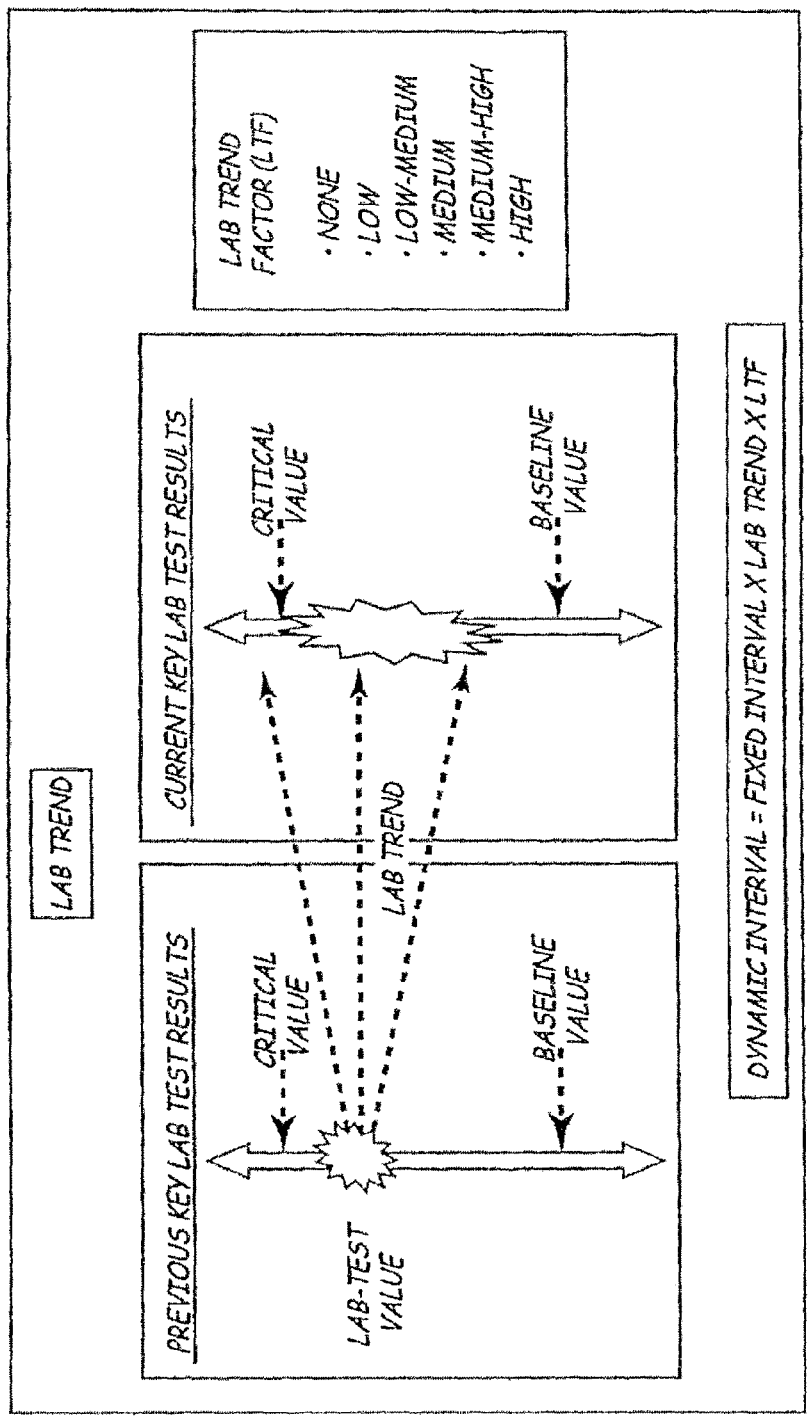
FIG. 9 is a diagram of an alternate embodiment for calculating a dynamic interval.

As shown in FIGS. 8 and 9, in one embodiment the two dynamic response time modifiers are "Lab Criticality" and "Lab Trend". The Lab Criticality modifier considers the current Target Lab test result compared to the abnormal and critical lab values defined within the Rule. The closer the current lab test is to the critical lab value, the shorter the response interval. The Lab Trend modifier considers the current Target Lab test as compared to the previous result for the same lab test. If the Target Lab results are improving, then the response time interval is extended based upon the Lab Trend modifier. If however, the lab results are getting worse, the Lab trend modifier is used to shorten the response interval time.

E. Patient Care Monitoring

As shown in FIGS. 1, 4, and 7, in one embodiment, Patient Care monitoring is performed by receiving data from a health care practitioner's laboratory 26 and pharmacy 24 information systems and then integrating and correlating the data. The Practice Guidelines Search Engine receives this data and searches the Practice Guidelines Rule. Database 12 to see if a Rule Criterion 40 is satisfied. The search engine can be any known in the art and which performs in a known manner.

In one embodiment, each Practice Guideline Rule defines a Target Lab condition or a Target Drug condition. Lab Practice Guidelines and Drug Practice Guidelines are handled differently. In order to minimally satisfy a Lab Practice Guideline, a Target Lab test must have been taken, and the result of that test must be within a pre-defined range. To minimally satisfy a Drug Practice Guideline, a Target Drug must have been ordered.

Once the Practice Guideline is minimally satisfied, the subject invention will then filter the patient data for associated drugs 50, associated labs 52, or additional filters 53. Each Practice Guideline Rule can specify that a patient must concurrently be on other medication or must have recently had specific lab tests with specific results. Also, the criteria located within the additional filters must also be satisfied before the Rule Criterion 40 can be fully satisfied. These additional filters 53 can be used to narrow a Practice Guideline Rule to a specific patient characteristic, a specific location within a health care facility, or a specific doctor. Through the use of associated drugs 50, labs 52, and additional filters 53, each Practice Guideline Rule can be defined to address very sophisticated conditions.

Once the Rule Criterion 40 are satisfied, the Patient Care Monitoring System 10 establishes a Practice Interval to wait for the expected clinical response. During this Practice Interval, the subject invention monitors for new drug orders and lab tests for the patient. If the new drug orders and lab tests satisfy the Response Criteria for the patient, then no Reminder is issued. If however, nearing the end of the interval, the correct drug orders and lab tests have not been performed, then a Reminder is issued.

As shown in FIG. 8, in one embodiment, the Practice Interval 44 can be changed dynamically to account for the criticality of a particular lab result. The Practice Interval 44 is changed in relation to the criticality of the value of the latest lab test. This criticality is determined as a percentage of the distance between a critical value of a lab test and a baseline value of the test. The Practice Interval 44 is also weighted in relation to a predetermined criticality factor assigned to the lab test. The Practice Interval 44 is then multiplied by the lab criticality and the lab criticality factor to determine a time interval for a particular rule.

As shown in FIG. 9, in one embodiment, the Practice Interval 44 is also changed dynamically to account for trends in the patient's lab results. A weighting for a trend is given based on the values of previous lab results in relation to a critical value and a baseline value. This weighting is then factored in with a predetermined lab trend factor assigned to the lab test. The Practice Interval 44 is then multiplied with the weighted value of the lab trend and with the lab trend factor to determine a time interval for a particular rule.

In one embodiment, Reminders are assigned a low, medium or high priority. The level of priority may be based upon the danger rating of the guideline not being followed and is set by the user when the rule is created or modified. The Reminder may also based upon the value of the most recent lab test or the failure to order a certain drug that is indicated in a specific situation.

In one embodiment, the priority level is handled differently for Drug Practice Guideline Rules than for Lab Practice Guideline Rules. For Drug Practice Guideline Rules, a variable priority level is not available. All Drug Practice Guideline Notifications are assigned a Priority of "High". For Lab Practice Guideline Rules, the priority is dynamically determined based upon the Target Lab test result value. The closer the Target Lab value to the critical level, the higher the priority.

In one embodiment, the subject invention includes Reminder management tools that enable authorized users to view reminders by status condition. In addition, authorized users can acknowledge Reminders and include comments about them. These will typically involve the use of a computer in communication with the central processor 12 and a display. Using the report generation software 40, a user can track the progression of a Reminder from when it was issued, to who viewed it, and to when it was acknowledged.

In certain situations, it may be appropriate to immediately notify the clinical staff of a Reminder. In one embodiment, the central processor 20 can be interfaced to communicate in a known manner to a plurality of alert systems such as a paging system, or an E-mail system, or a central computer located within the health care facility.

Patient Care Monitoring can be done in real time by having the medical facility transmit applicable data as soon as it is received, and by having Patient Care Monitoring activated automatically upon reception of new laboratory and pharmacy data. Real time Patient Care Monitoring allows nearly instantaneous detection of deviations from Practice Guideline Rules. The Patient Care Monitoring System 10 can also be activated periodically by allowing transmitted pharmacy and lab data to accumulate in pharmacy 56 and laboratory 57 databases and searching for matches at predefined times, or upon activation by a user.

F. Patient Reports

Since the subject invention captures all drug orders and lab test results, it contains a wealth of information that can be mined and analyzed. This data can be used for research purposes, as well as for quality and risk management. Authorized hospital staff has online access to view current as well as historical Reminders issued. In addition, the subject invention provides a comprehensive reporting capability. Various reports can be printed for historical analysis and assessment.

The Patient Care Monitoring System 10 stores data received from the medical facility, as well as the reminders which are generated in a database which is accessible to users for patient care, quality assurance, or medical research. Information within the database can be filtered and compiled by a user to provide specific information relating to a particular patient or to a number of patients within a medical facility. The information can be filtered and compiled via criteria determined through an interactive query or through predefined report parameters.

In another embodiment, the Patient Care Monitoring System 10 includes a report generation application 38 which can generate predefined reports such as a system report which compiles predefined data for an entire system. These reports are predefined and can be generated by simply selecting the function from a menu.

While the present invention has been described with reference to several embodiments thereof, those skilled in the art will recognize various changes that may be made without departing from the spirit and scope of the claimed invention. Accordingly, this invention is not limited to what is shown in the drawings and described in the specification but only as indicated in the appended claims, nor is the claimed invention limited in applicability to one type of computer or computer network. Any numbering or ordering of elements in the following claims is merely for convenience and is not intended to suggest that the ordering of the elements of the claims has any particular significance other than that otherwise expressed by the language of the claim.

Although the present invention has been described with reference to preferred embodiments, persons skilled in the art will recognize that changes may be made in form and detail without departing from the spirit and scope of the invention.

We claim:

1. A method for monitoring care in a computer-implemented system, comprising:
   a) accessing a rule criterion, the rule criterion comprising a plurality of conditions;
   b) accessing a response criterion, the response criterion comprising a plurality of responses;
   c) receiving data comprising at least one target event having a current value;
   d) analyzing the data according to the rule criterion and the response criterion;
   e) generating a practice interval having a defined length of time that is determined based upon the response criterion and the data;
   f) dynamically adjusting the practice interval based on the data:
      wherein the practice interval is dynamically adjusted based upon a criticality of the data or based upon one or more trends indicated by the data,
      wherein the criticality is determined as a percentage of the distance between a critical value of the target event and a baseline value of the target event and weighted in relation to a predetermined criticality factor pertaining to the target event, and
      wherein a trend indicated by the data is determined based upon a value of one or more previously received at least one target event, if any, the critical value of the target event, the baseline value of the target event, and a predetermined trend factor pertaining to the target event; and
   g) generating a reminder notification if the data does not satisfy the response criterion within the practice interval,
   wherein the accessing, receiving, analyzing, and generating functions are performed by the computer-implemented system.

2. A system for monitoring care, comprising:
   a) a first data source, the first data source comprising a rule criteria, the rule criteria comprising a plurality of conditions; and the first data source further comprising a response criteria, the response criteria comprising a plurality of responses;
   b) a second data source for receiving data comprising at least one target event;
   c) a central processor configured to communicate with the first data source and the second data source;
   wherein the central processor is further configured to analyze the data according to the rule criterion and the response criterion, generate a practice interval having a defined length of time that is determined based upon the response criterion and the data, and generate a reminder notification if the data does not satisfy the response criterion within the practice interval, and
   wherein the practice interval is configured to be dynamically adjusted by the central processor based upon a criticality of the data or based upon one or more trends indicated by the data, wherein the criticality is determined as a percentage of the distance between a critical value of the target event and a baseline value of the target event and weighted in relation to a predetermined criticality factor pertaining to the target event, and wherein a trend indicated by the data is determined based upon a value of one or more previously received at least one target event, if any, the critical value of the target event, the baseline value of the target event, and a predetermined trend factor pertaining to the target event.

3. A non-transitory computer program product, comprising:
   a) a computer usable medium, the computer usable medium having embodied thereon a computer readable program code comprising instructions to cause a computer to:
      1) access a first data source, the first data source comprising a rule criteria, the rule criteria comprising a plurality of conditions, and the first data source further comprising a response criteria, the response criteria comprising a plurality of responses;
2) access a second data source for receiving data comprising at least one target event;
3) analyze the data according to the rule criterion and the response criterion;
4) generate a practice interval having a defined length of time that is determined based upon the response criterion and the data; and
5) generate a reminder notification if the data does not satisfy the response criterion within the practice interval, wherein the practice interval is dynamically adjustable based upon a criticality of the data or based upon one or more trends indicated by the data, wherein the criticality is determined as a percentage of the distance between a critical value of the target event and a baseline value of the target event and weighted in relation to a predetermined criticality factor pertaining to the target event, and wherein a trend indicated by the data is determined based upon a value of one or more previously received at least one target event, if any, the critical value of the target event, the baseline value of the target event, and a predetermined trend factor pertaining to the target event.

* * * * *